(12) United States Patent
Shiu et al.

(10) Patent No.: US 6,911,039 B2
(45) Date of Patent: Jun. 28, 2005

(54) INTEGRATED MECHANICAL HANDLE WITH QUICK SLIDE MECHANISM

(75) Inventors: Brian Shiu, Sunnyvale, CA (US); Ari Gershman, Moraga, CA (US); Burt Goodson, Fremont, CA (US)

(73) Assignee: Medtronic Vascular, Inc., Santa Clara, CA (US)

( * ) Notice: Subject to any disclaimer, the term of this patent is extended or adjusted under 35 U.S.C. 154(b) by 0 days.

(21) Appl. No.: 10/128,956

(22) Filed: Apr. 23, 2002

(65) Prior Publication Data

US 2003/0199966 A1 Oct. 23, 2003

(51) Int. Cl.[7] .................................................. A61F 2/06
(52) U.S. Cl. ................................... 623/1.12; 623/1.23
(58) Field of Search .............................. 623/1.11, 1.12, 623/1.23; 606/108; 604/95.05, 104, 105, 106, 107, 108, 109, 523, 533, 534, 535, 537

(56) References Cited

U.S. PATENT DOCUMENTS

| | | | |
|---|---|---|---|
| 1,827,497 A | 10/1931 | Varney | |
| 4,723,938 A | 2/1988 | Goodin | |
| 4,832,692 A * | 5/1989 | Box et al. ................. | 604/99.01 |
| 5,137,514 A * | 8/1992 | Ryan ........................ | 604/99.01 |
| 5,197,971 A | 3/1993 | Bonutti | |
| 5,215,523 A * | 6/1993 | Williams et al. .......... | 604/97.03 |
| 5,259,838 A | 11/1993 | Taylor et al. | |
| 5,263,969 A | 11/1993 | Phillips | |
| 5,344,426 A | 9/1994 | Lau et al. | |
| 5,345,927 A | 9/1994 | Bonutti | |
| 5,353,496 A | 10/1994 | Harman et al. | |
| 5,433,723 A | 7/1995 | Lindenberg et al. | |
| 5,449,344 A | 9/1995 | Taylor et al. | |
| 5,462,659 A * | 10/1995 | Saxena et al. ........... | 210/198.2 |
| 5,507,727 A | 4/1996 | Crainich | |
| 5,507,768 A | 4/1996 | Lau et al. | |
| 5,534,007 A | 7/1996 | St. Germain | |
| 5,571,168 A | 11/1996 | Toro | |
| 5,683,451 A * | 11/1997 | Lenker et al. ............. | 623/1.11 |
| 5,707,376 A | 1/1998 | Kavteladze et al. | |
| 5,733,267 A | 3/1998 | Del Toro | |
| 5,776,142 A | 7/1998 | Gunderson | |
| 5,788,707 A | 8/1998 | Del Toro | |
| 5,797,952 A | 8/1998 | Klein | |
| 5,824,058 A | 10/1998 | Ravenscroft | |
| 5,860,955 A * | 1/1999 | Wright et al. ............ | 604/99.01 |
| 5,906,619 A * | 5/1999 | Olson et al. ................ | 606/108 |
| 5,954,742 A | 9/1999 | Osypka | |
| 5,968,052 A | 10/1999 | Sullivan et al. | |
| 6,042,588 A | 3/2000 | Munsinger et al. | |
| 6,117,142 A * | 9/2000 | Goodson et al. ........... | 606/108 |
| 6,146,415 A | 11/2000 | Fitz | |
| 6,203,550 B1 | 3/2001 | Olson | |
| 6,508,790 B1 * | 1/2003 | Lawrence ............... | 604/167.05 |
| 2002/0004676 A1 | 1/2002 | Berryman et al. | |
| 2002/0111666 A1 | 8/2002 | Hart et al. | |
| 2003/0074043 A1 * | 4/2003 | Thompson ................ | 623/1.11 |

FOREIGN PATENT DOCUMENTS

EP         1117341        7/2001

* cited by examiner

*Primary Examiner*—Corrine McDermott
*Assistant Examiner*—Thomas J Sweet

(57) ABSTRACT

A method of deploying a prosthesis includes restraining the prosthesis within a distal end of a sheath. A slide ring of a handle is rotated to initiate retraction of the sheath. In this manner, the prosthesis is initially very gradually released. The slide ring is then slid to complete retraction of the sheath and to deploy the prosthesis. In this manner, the sheath is easily and quickly retracted thus rapidly completing deployment of the prosthesis. Rapid deployment of the prosthesis facilitates faster procedure times, thus minimizing the period of time during which blood flow is occluded.

48 Claims, 7 Drawing Sheets

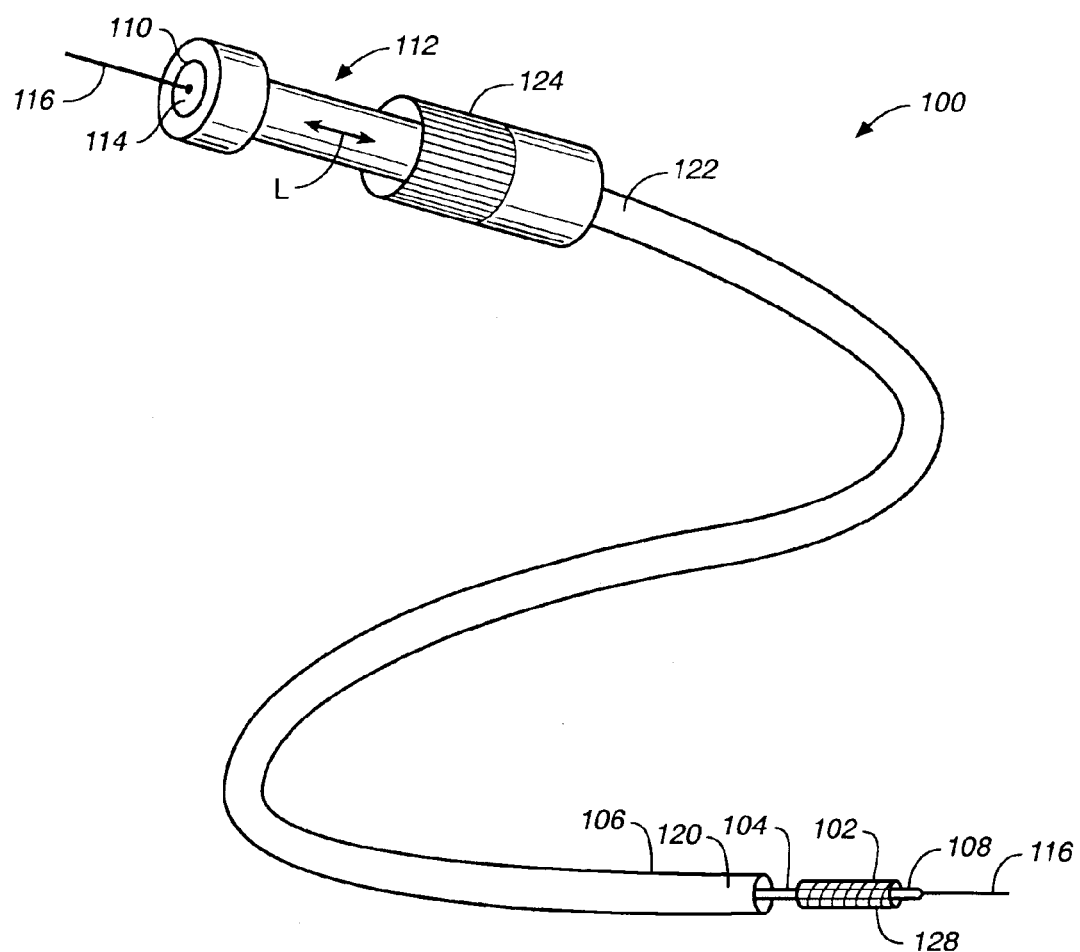
FIG._1

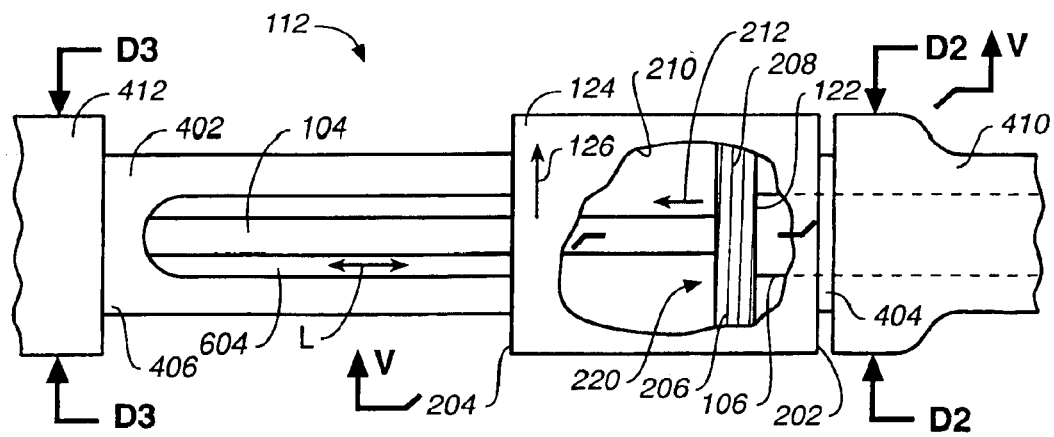
FIG._2
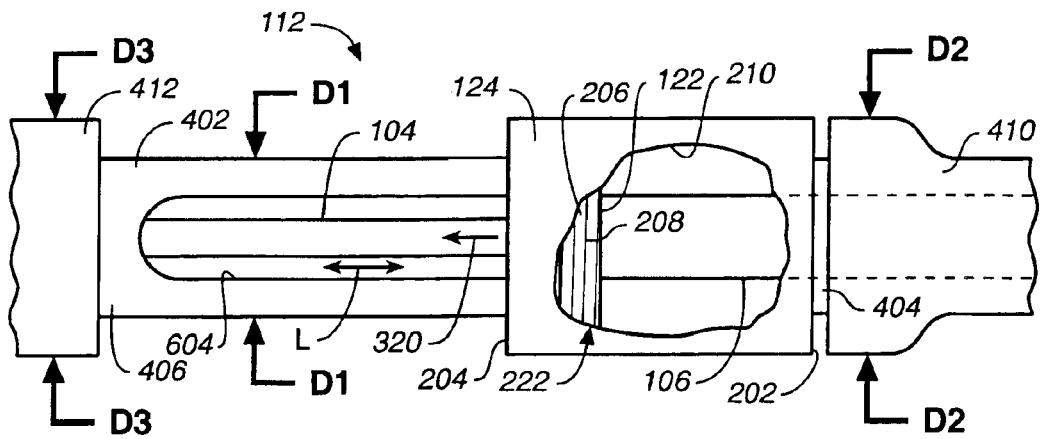
FIG._3
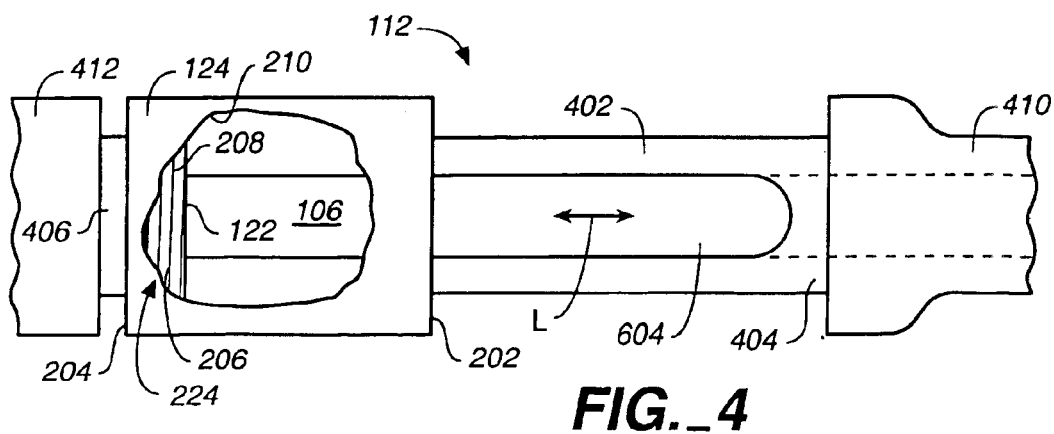
FIG._4

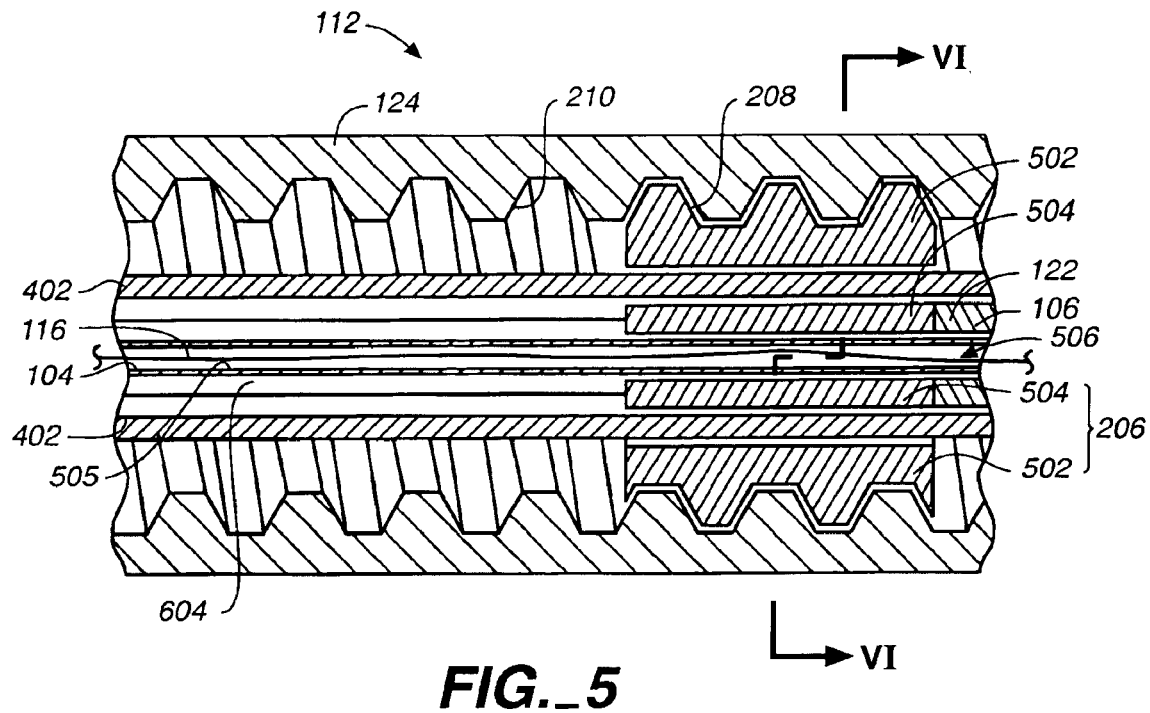
FIG._5
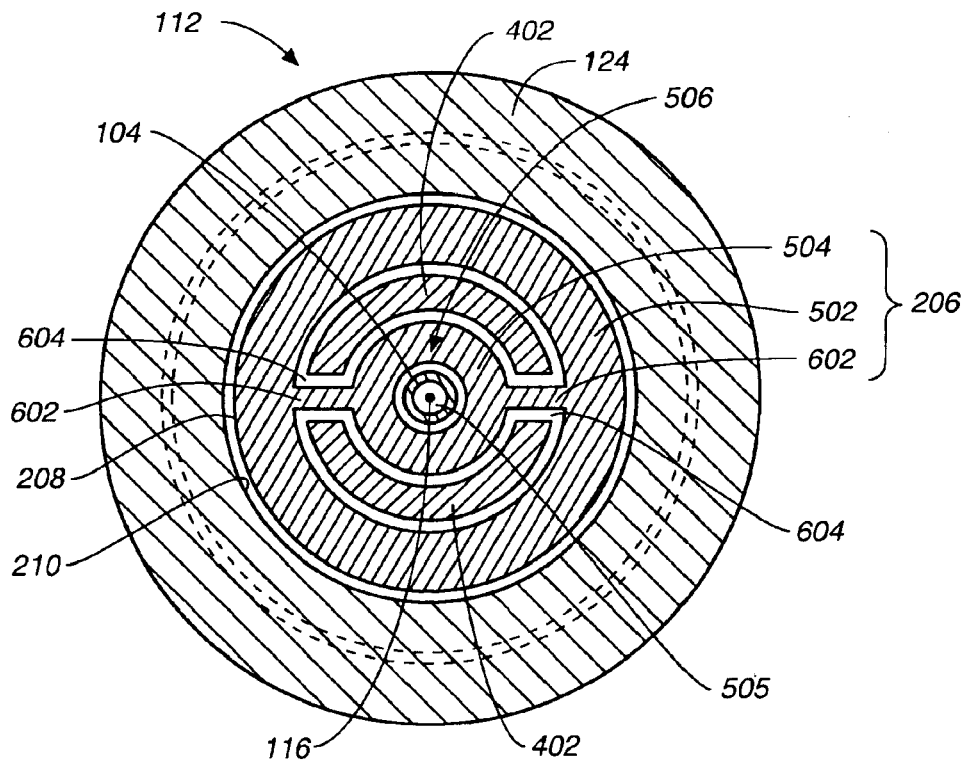
FIG._6

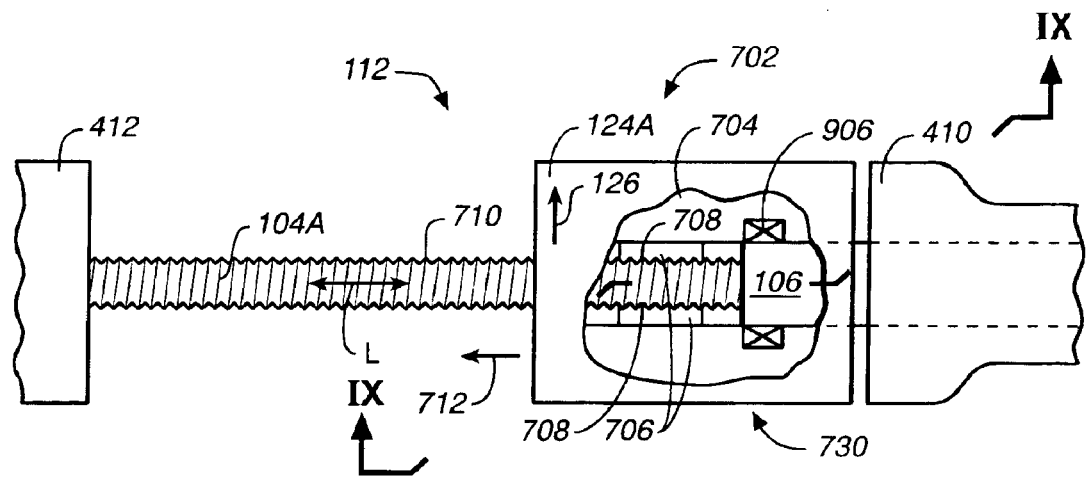
FIG._7
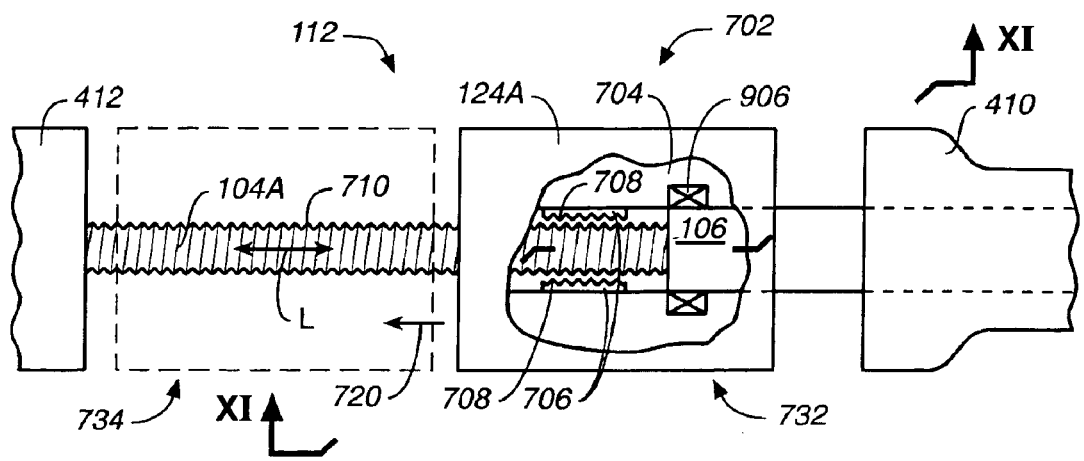
FIG._8

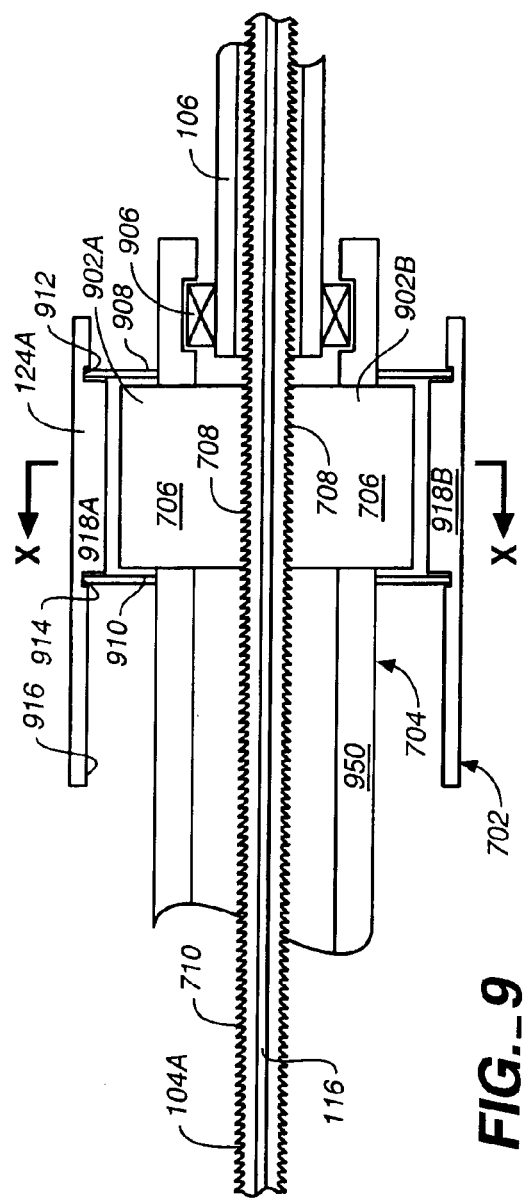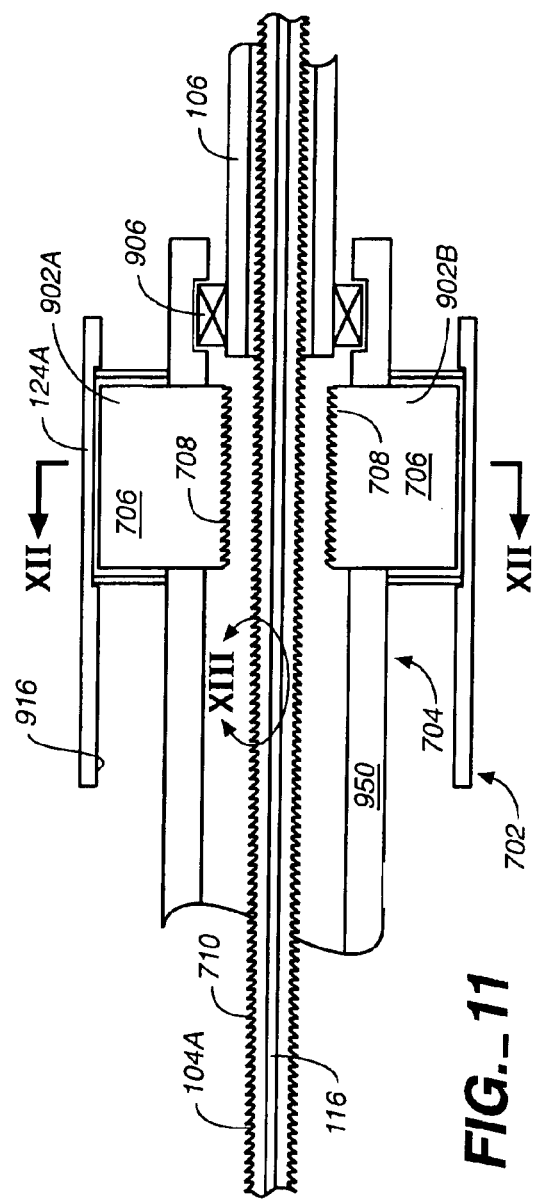

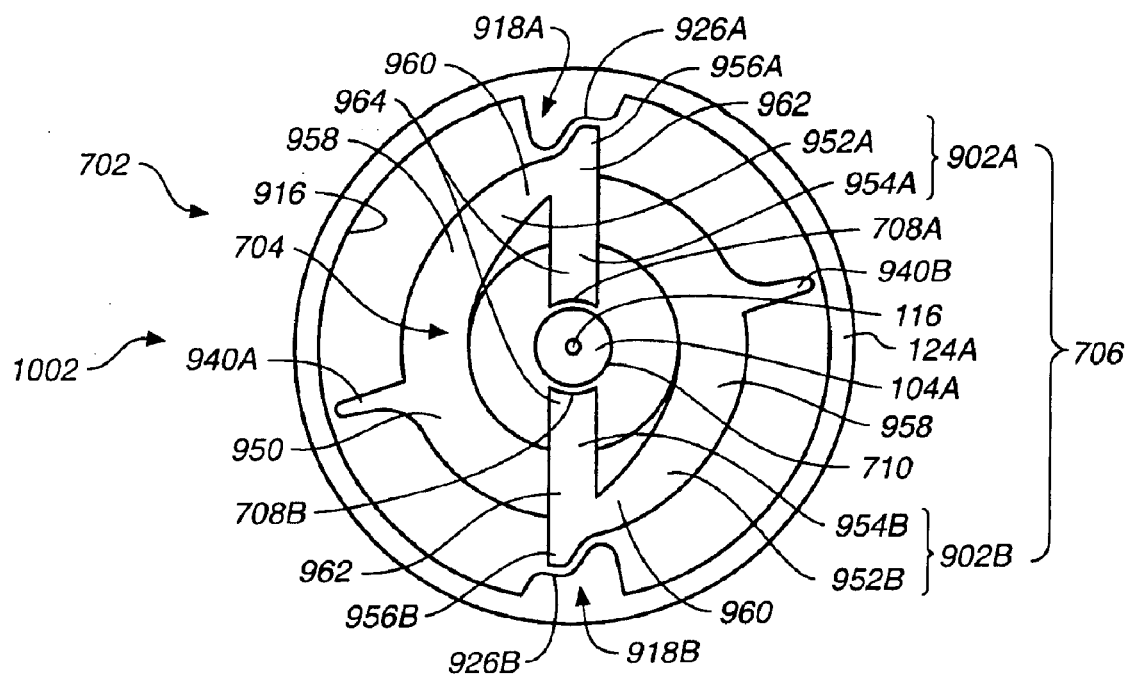
FIG._10
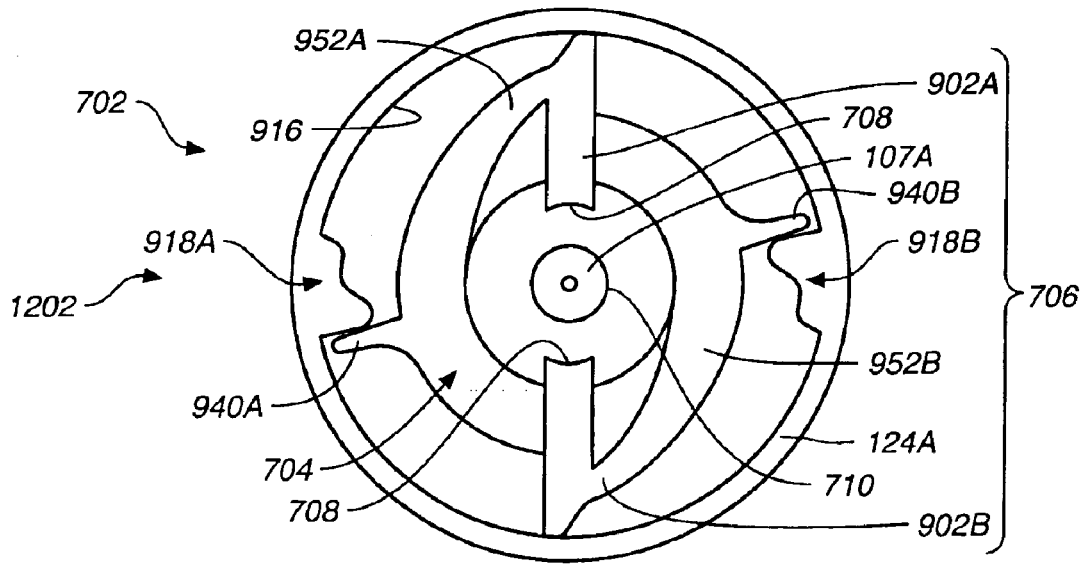
FIG._12

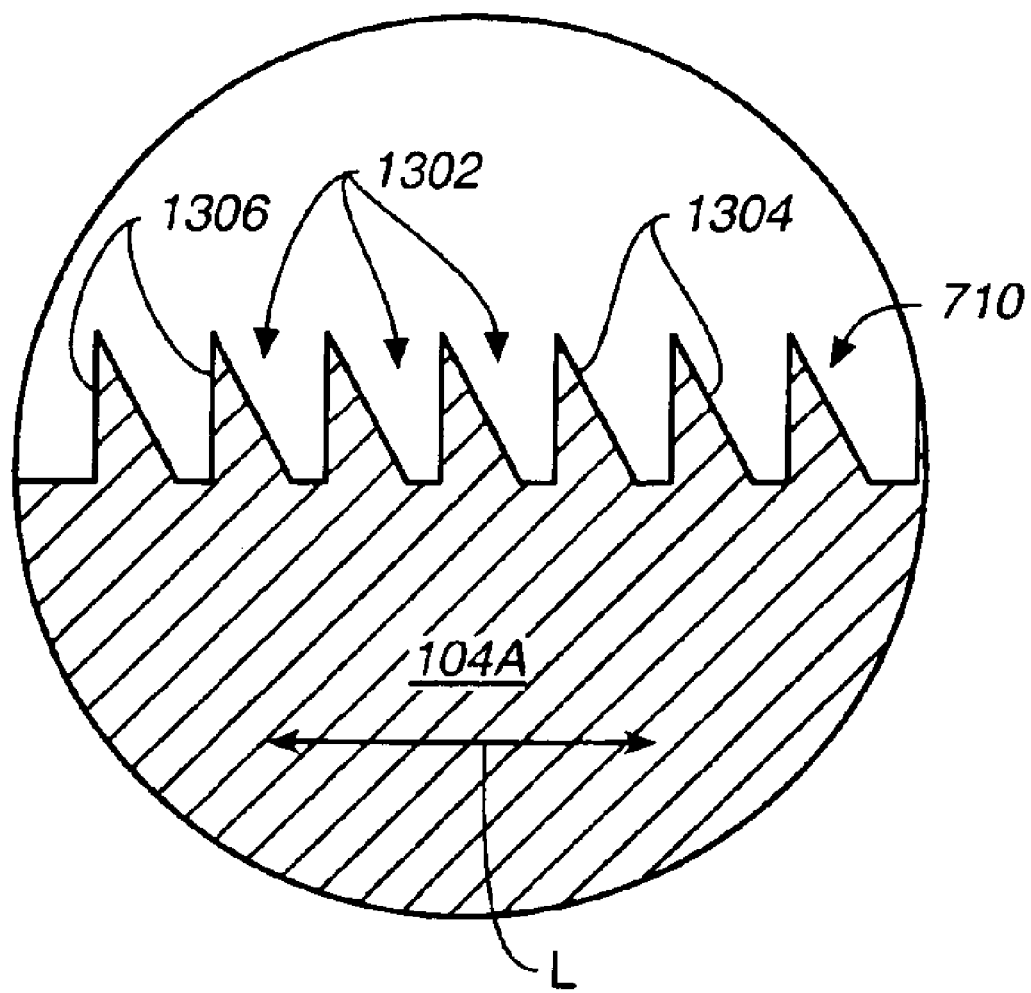
FIG._13

INTEGRATED MECHANICAL HANDLE WITH QUICK SLIDE MECHANISM

BACKGROUND OF THE INVENTION

1. Field of the Invention

The present invention relates to an intra-vascular device and method. More particularly, the present invention relates to a delivery system for deploying endoluminal prostheses within the lumens of the body and to a method of using the same.

2. Description of the Related Art

Vascular aneurysms were the result of abnormal dilation of a blood vessel, usually resulting from disease and/or genetic predisposition, which weakened the arterial wall and allowed it to expand. While aneurysms could occur in any blood vessel, most occurred in the aorta and peripheral arteries, with the majority of aortic aneurysms occurring in the abdominal aorta, usually beginning below the renal arteries and often extending into one or both of the iliac arteries.

Aortic aneurysms were commonly treated in open surgical procedures where the diseased vessel segment was bypassed and repaired with an artificial vascular graft. While considered to be an effective surgical technique, particularly considering the alternative of a usual fatal ruptured abdominal aortic aneurysm, conventional vascular graft surgery suffered from a number of disadvantages. The surgical procedure was complex and required experienced surgeons and well-equipped surgical facilities. Even with the best surgeons and equipment, however, patients being treated frequently were elderly and weakened from cardiovascular and other diseases, reducing the number of eligible patients.

Even for eligible patients prior to rupture, conventional aneurysm repair had a relatively high mortality rate, usually from 2% to 10%. Morbidity related to the conventional surgery includes myocardial infarction, renal failure, impotence, paralysis, and other conditions. Additionally, even with successful surgery, recovery took several weeks, and often required a lengthy hospital stay.

In order to overcome some or all of these drawbacks, endovascular prosthesis placement for the treatment of aneurysms has been used. Although very promising, many of the proposed methods and apparatus suffered from undesirable limitations. In particular, accurate delivery and placement of the endovascular prosthesis within the vasculature was problematic.

Stent-grafts (endovascular prosthesis) are resilient structures, usually biased to expand against the surrounding lumenal wall. Such resiliently-expanding stent-grafts were tightly compressed within the catheter, imposing significant radial expansion forces against the surrounding catheter sheath. This often lead to excess friction between the stent-graft and the sheath, particularly when the resiliently-expanding structure invaginated into the catheter material. Thus, the delivery system had to be capable of imparting a significant, yet controlled, force to retract the sheath and deploy the stent-grafts.

SUMMARY OF THE INVENTION

In accordance with an embodiment of the present invention, a method of deploying a prosthesis includes restraining the prosthesis within a distal end of a sheath. A slide ring of a handle engaged with threads in the handle is rotated in a first direction to initiate a force for the retraction of the sheath. The slide ring is slid to complete retraction of the sheath and deploy the prosthesis.

As a result, a proximal end of the prosthesis, which is deployed first, is very gradually released by rotating the slide ring. In this manner, the physician is allowed to verify the accuracy of the deployment position as the prosthesis initially engages the surrounding body lumen.

However, since dynamic frictional forces are typically lower than static frictional forces, the frictional resistance, due to the forces between the prosthesis and the sheath, decreases once the sheath begins to move. Additionally, as the sheath moves (retracts), more and more of the prosthesis is exposed by the sheath. For this additional reason, the frictional resistance, due to the force between the prosthesis and the sheath, decreases once the sheath begins to move. Further, once the proximal end of the prosthesis has firmly engaged the surrounding body lumen, the relationship between the prosthesis and the surrounding body lumen is largely set, so that deployment can proceed safely and at a more rapid rate.

Thus, after retraction of the sheath is initiated by axial rotation of the slide ring, which moves axially because of the engagement of threaded pieces, the sheath is further retracted by sliding (manual pulling) of the slide ring. By sliding the slide ring, the sheath is easily and quickly retracted thus rapidly completing deployment of the prosthesis. Rapid deployment of the prosthesis facilitates faster procedure times, thus minimizing the period of time during which blood flow is occluded.

In accordance with another embodiment of the present invention, a delivery system includes a handle and a sheath slidably and threadedly coupled to the handle.

In accordance with yet another embodiment of the present invention, a delivery system includes a handle having: a slide shaft having at least one slot; a slide ring; a slide threadedly attached to the slide ring, the slide having: an inner body inside the slide shaft; an outer body outside the slide shaft; and a coupler coupling the inner body to the outer body through the at least one slot, wherein the slide ring and the slide are slidably mounted to the slide shaft.

In accordance with another embodiment, a delivery system includes: a sheath having a pushrod lumen; a pushrod extending through the sheath; and a handle having a hub assembly coupled to the sheath, the hub assembly having a selectively engaging member for selectively engaging and disengaging the hub assembly from the pushrod.

The present invention is best understood by reference to the following detailed description when read in conjunction with the accompanying drawings.

BRIEF DESCRIPTION OF THE DRAWINGS

FIG. 1 is a perspective view of a delivery system for deploying a prosthesis in accordance with one embodiment of the present invention;

FIG. 2 is a close up partial cutaway view of a handle of FIG. 1 before retraction of a sheath;

FIGS. 3 and 4 are close up partial cutaway views of the handle of FIG. 2 during retraction of the sheath in accordance with one or more embodiments of the present invention;

FIG. 5 is a partial cross-sectional view of the handle taken at V—V of FIG. 2;

FIG. 6 is a cross-sectional view of the handle taken at VI—VI of FIG. 5;

FIG. 7 is a close up partial cutaway view of the handle of FIG. 1 before retraction of the sheath in accordance with another embodiment of the present invention;

FIG. 8 is a close up partial cutaway view of the handle of FIG. 7 during retraction of the sheath;

FIG. 9 is a cross-sectional view of the handle of FIG. 7 taken at IX—IX;

FIG. 10 is a cross-sectional view of the handle taken at X—X of FIG. 9 in accordance with one embodiment of the present invention;

FIG. 11 is a cross-sectional view of the handle taken at XI—XI of FIG. 8 in accordance with one embodiment of the present invention;

FIG. 12 is a cross-sectional view of the handle taken at XII—XII of FIG. 11 in accordance with one embodiment of the present invention; and FIG. 13 is an enlarged cross-sectional view of region XIII of a pushrod of FIG. 11 in accordance with one embodiment of the present invention.

Common reference numerals are used throughout the drawings and detailed description to indicate like elements.

DETAILED DESCRIPTION

In accordance with one embodiment of the present invention, a method of deploying a prosthesis 102 (FIG. 1) includes restraining prosthesis 102 within a distal end 120 of a sheath 106. A slide ring 124 of a handle 112 is rotated in a first direction as indicated by an arrow 126 (FIG. 2) to initiate retraction of sheath 106. Slide ring 124 is slid (FIGS. 3, 4) to complete retraction of sheath 106 and deploy prosthesis 102 (FIG. 1)

In this manner, prosthesis 102 is initially very gradually released by rotating slide ring 124. This allows the physician to verify the accuracy of the deployment position as prosthesis 102 initially engages the surrounding body lumen.

However, after retraction of sheath 106 is initiated by rotation of slide ring 124 with respect to handle 112, retraction of sheath 106 is completed by sliding of slide ring 124 along the longitudinal axis of handle 112. In this manner, sheath 106 is easily and quickly retracted thus rapidly completing deployment of prosthesis 102. Rapid deployment of prosthesis 102 facilitates faster procedure times, thus minimizing the period of time during which blood flow is occluded.

More particularly, FIG. 1 is a perspective view of a delivery system 100 for deploying a prosthesis 102 in accordance with one embodiment of the present invention. For example, prosthesis 102 is a radially expandable tubular prosthesis such as a stent or stent-graft.

Delivery system 100 includes a pushrod 104 and a sheath 106, sometimes called a catheter sheath. Pushrod 104 includes a distal end 108 and a proximal end 110. Prosthesis 102 is placed over distal end 108 of pushrod 104. In one embodiment, distal end 108 further includes radiopaque markers that allow the location of distal end 108 and prosthesis 102 to be precisely tracked. Proximal end 110 of pushrod 104 terminates within and is mounted to a handle 112 or extends through handle 112 and out a port 114 of handle 112.

In this embodiment, pushrod 104 is a hollow tube and includes a guide wire lumen. A guide wire 116 extends through pushrod 104 and extends out distal end 108. Guide wire 116 further extends through handle 112 and out port 114.

Sheath 106 includes a distal end 120 and a proximal end 122. Prior to deployment, prosthesis 102 is radially compressed and restrained within distal end 120 of sheath 106. Proximal end 122 of sheath 106 extends into handle 112. As discussed further below, proximal end 122 of sheath 106 is slidably and threadedly coupled to handle 112. Sheath 106 is a hollow tube and includes a pushrod lumen. Pushrod 104 extends through sheath 106.

During use, prosthesis 102 is placed over distal end 108 of pushrod 104 and is radially compressed and restrained within distal end 120 of sheath 106. Prosthesis 102 is introduced intra-vascularly and guided to the treatment site, e.g., an aneurysm. Once prosthesis 102 is properly positioned, sheath 106 is retracted by manipulating handle 112 thus deploying prosthesis 102.

In one embodiment, prosthesis 102 is self-expandable. In accordance with this embodiment, as sheath 106 is retracted, prosthesis 102 self-expands and is permanently deployed, e.g., anchored within a lumen of a patient.

The guiding of prosthesis and deployment of a self-expanding prosthesis are well known to those of skill in the art.

FIG. 2 is a close up partial cutaway view of handle 112 of FIG. 1 before retraction of sheath 106 in accordance with one embodiment of the present invention. Referring now to FIGS. 1 and 2 together, handle 112 includes a slide ring 124. Rotation of slide ring 124 with respect to longitudinal axis L of handle 112 (axial rotation) as indicated by arrow 126 is converted into axial translation, i.e., retraction, of sheath 106. This provides a mechanical advantage between handle 112 and sheath 106, helping the physician to overcome the large static frictional forces between prosthesis 102 and sheath 106. This mechanical advantage also helps overcome any invagination of prosthesis 102 into sheath 106.

FIG. 3 is a close up partial cutaway view of handle 112 of FIG. 2 during retraction of sheath 106 in accordance with one embodiment of the present invention. Referring now to FIGS. 2 and 3 together, slide ring 124 includes a distal end 202 and a proximal end 204. Located within and coupled to slide ring 124 is a slide 206. In one embodiment, slide 206 includes a threaded outer surface 208 threadedly attached to a threaded inner surface 210 of slide ring 124.

Initially, slide 206 is located adjacent distal end 202 of slide ring 124 as illustrated in FIG. 2. Axial rotation of slide ring 124 as indicated by arrow 126 causes axial translation of slide 206 as indicated by arrow 212 away from distal end 202 and towards proximal end 204 of slide ring 124.

Handle 112 includes a longitudinal axis L. As used herein, axial rotation is rotation around and in a plane perpendicular to longitudinal axis L. Further, axial translation is motion along longitudinal axis L. Axial position is a particular position along longitudinal axis L. Angular position is a particular rotational position around and in a plane perpendicular to longitudinal axis L.

For example, slide 206 is illustrated as being in a first axial position 220 adjacent distal end 202 of slide ring 124 in FIG. 2. Axial rotation of slide ring 124 as indicated by arrow 126 causes slide 2.06 to move to a second axial position 222 adjacent proximal end 204 of slide ring 124 as illustrated in FIG. 3.

Sheath 106 is coupled to slide 206 as discussed further below. Accordingly, axial translation of slide 206 is converted into axial translation, i.e., retraction, of sheath 106.

As a result, referring again to FIG. 1, a proximal end 128 of prosthesis 102, which is deployed first, is very gradually released. In this manner, the physician is allowed to verify the accuracy of the deployment position as prosthesis 102 initially engages the surrounding body lumen.

However, since the coefficient of dynamic friction is typically lower than the coefficient of static friction, the frictional resistance force between prosthesis 102 and sheath 106 decreases once sheath 106 begins to move. Additionally, as sheath 106 moves, more and more of prosthesis 102 is exposed by sheath 106, i.e., the area of contact between prosthesis 102 and sheath 106 decreases. For this additional reason, the amount of frictional resistance to movement between prosthesis 102 and sheath 106 decreases once sheath 106 begins to move. Further, once proximal end 128 of prosthesis 102 has firmly engaged the surrounding body lumen, the relationship between prosthesis 102 and the surrounding body lumen is largely set, so that deployment can proceed safely and at a more rapid rate.

Thus, after retraction of sheath 106 is initiated by axial rotation of slide ring 124, retraction of sheath 106 is completed by axially pulling on slide ring 124 to slide slide ring 124. More particularly, after proximal end 128 of prosthesis 102 is deployed by retracting sheath 106 by rotating slide ring 124, slide ring 124 is easily and quickly slid along longitudinal axis L of handle 112 without further axial rotation of slide ring 124. By sliding slide ring 124, sheath 106 is easily and quickly retracted thus rapidly completing deployment of prosthesis 102. Rapid deployment of prosthesis 102 facilitates faster procedure times, thus minimizing the period of time during which blood flow is occluded.

Sheath 106 is described above as being retracted by the combination of axial rotation of slide ring 124 followed by axial translation, i.e., sliding, of slide ring 124 along longitudinal axis L of handle 112. However, in an alternative embodiment, sheath 106 is retracted entirely by axial rotation of slide ring 124. Further, in yet another alternative embodiment, sheath 106 is retracted entirely by sliding of slide ring 124 along longitudinal axis L of handle 112.

FIG. 4 is a close up partial cutaway view of handle 112 of FIG. 3 during retraction of sheath 106 in accordance with one embodiment of the present invention. Referring now to FIGS. 3 and 4 together, handle 112 includes a slide shaft 402 having a distal end 404 and a proximal end 406. Slide shaft 402 extends between a distal housing 410 and a proximal housing 412 of handle 112. Slide 206 and slide ring 124 are slidably mounted on slide shaft 402.

A diameter D1 of slide shaft 402 is less than a distal end diameter D2 of distal housing 410 and is less than a diameter D3 of proximal housing 412. Accordingly, slide ring 124 is capable of axial translation along slide shaft 402 between distal housing 410 and proximal housing 412. Stated another way, distal housing 410 forms a forward stop for slide ring 124 and proximal housing 412 forms a rear stop for slide ring 124.

Slide ring 124 is easily and quickly slid along slide shaft 402 of handle 112 from distal housing 410 to proximal housing 412. Since slide 206 is threadedly engaged with (sometimes called threadedly attached) to slide ring 124, axial translation of slide ring 124 produces an axial translation of slide 206. Since slide 206 is coupled to sheath 106, axial translation of slide 206 produces an axial translation of sheath 106. Overall, by sliding slide ring 124, sheath 106 is easily and quickly retracted thus rapidly completing deployment of prosthesis 102.

For example, slide ring 124 is illustrated as being adjacent distal housing 410 of handle 112 in FIG. 3. Axial translation of slide ring 124 as indicated by arrow 320 causes slide ring 124 and slide 206 to move to a third axial position 224 adjacent proximal housing 412 of handle 112 as illustrated in FIG. 4. Sheath 106 is coupled to slide 206. Accordingly, axial translation of slide ring 124 also axially translates, i.e., retracts, sheath 106.

FIG. 5 is a partial cross-sectional view of handle 112 taken at V—V of FIG. 2. FIG. 6 is a cross-sectional view of handle 112 taken at VI—VI of FIG. 5.

In one embodiment, slide ring 124 includes at least two sections joined together. However, in an alternative embodiment, slide ring 124 is integral, i.e., is a single piece not a plurality of pieces connected together.

Referring now to FIGS. 5 and 6 together, slide ring 124 is cylindrical and includes threaded inner surface 210. In one embodiment, threaded inner surface 210 is a cylindrical surface formed with a continuous thread (sometimes called a series of threads), e.g., internal threads.

Slide 206 includes an outer body 502, an inner body 504, and couplers 602, which couple outer body 502 to inner body 504 as discussed further below. In one embodiment, outer body 502 is cylindrical and is outside and encloses slide shaft 402, which is also cylindrical.

Outer body 502 includes threaded outer surface 208. In one embodiment, threaded outer surface 208 is a cylindrical surface formed with a continuous thread (sometimes called a series of threads), e.g., external and helical threads. More particularly, threaded outer surface 208 is a cylindrical surface formed with a continuous series of high points which together form a helical thread pattern.

Threaded outer surface 208 of outer body 502 is threaded with threaded inner surface 210 of slide ring 124. More particularly, the external threads of threaded outer surface 208 are engaged with the internal threads of threaded inner surface 210 of slide ring 124. However, in alternative embodiments, threaded outer surface 208 can be formed with pins, tabs or other protrusions which mate (or engage) with the threads of threaded inner surface 210 of slide ring 124.

Rotation of slide ring 124 causes slide 206 to move along a helical path of the series of threads of threaded inner surface 210 of slide ring 124. More particularly, rotation of slide ring 124 causes threaded outer surface 208 of slide 206 to track the helical path of the series of threads of threaded inner surface 210 of slide ring 124. As threaded outer surface 208 of slide 206 tracks the helical path of the series of threads of threaded inner surface 210, slide 206 translates in direction 320 (FIG. 3) along longitudinal axis L.

Inner body 504 is inside and located within slide shaft 402. Inner body 504 includes a central aperture 506 through which pushrod 104 extends. Pushrod 104 includes a guide wire lumen 505 through which a guide wire 116 extends. Proximal end 122 of sheath 106 is attached to inner body 504, for example, using adhesive or screws.

Slide shaft 402 includes opposing slots 604. Couplers 602 extend through slots 604 and couple outer body 502 to inner body 504. By extending through slots 604, couplers 602 prevent rotation of slide 206 and thus of sheath 106 with respect to slide shaft 402.

In one embodiment, slide 206 is integral, i.e., outer body 502, inner body 504, and couplers 602 are parts of a single piece and are not a plurality of separate pieces connected together. However, in an alternative embodiment, outer body 502, inner body 504, and/or couplers 602 are separate pieces connected together. For example, couplers 602 can be set screws or tabs protruding radially inward or outward from outer body 502 and/or inner body 504, respectively.

FIG. 7 is a close up partial cutaway view of handle 112 of FIG. 1 before retraction of sheath 106 in accordance with another embodiment of the present invention. Referring now to FIGS. 1 and 7 together, handle 112 includes a hub assembly 702. Axial rotation of hub assembly 702 as indicated by arrow 126 is converted into axial translation, i.e., retraction, of sheath 106. This provides a mechanical advantage between handle 112 and sheath 106, helping the physician to overcome the relatively larger static frictional resistance between prosthesis 102 and sheath 106. This mechanical advantage also helps overcome any invagination of prosthesis 102 into sheath 106.

FIG. 8 is a close up partial cutaway view of handle 112 of FIG. 7 during retraction of sheath 106 in accordance with one embodiment of the present invention. Referring now to FIGS. 7 and 8 together, hub assembly 702 includes a slide ring 124A and a hub 704. Slide ring 124A, sometimes called a cam-lock ring, is mounted on hub 704. For example, slide ring 124A and hub 704 are molded parts fixedly mounted together.

Hub 704 includes a selectively engaging member 706. By rotating slide ring 124A, selectively engaging member 706 and thus hub assembly 702 is selectively engaged (FIG. 7) and disengaged (FIG. 8) from a pushrod 104A. To illustrate, in one embodiment, selectively engaging member 706 includes an inside threaded surface 708 and pushrod 104A includes a threaded outer surface 710, sometimes called an external threaded surface 710. In one embodiment, inside threaded surface 708 and external threaded surface 710 each include a continuous series of threads, e.g., helical threads. Stated another way, inside threaded surface 708 and external threaded surface 710 each are a continuous thread.

By rotating slide ring 124A in a first direction, e.g., counterclockwise, threaded surface 708 of selectively engaging member 706 is pressed into threaded engagement (attachment) with threaded outer surface 710 of pushrod 104A as illustrated in FIG. 7. Thus, rotation of slide ring 124A in the first direction engages selectively engaging member 706 with pushrod 104A. More generally, rotation of slide ring 124A in the first direction engages and threadably attaches (mounts) hub assembly 702 with pushrod 104A.

Initially, selectively engaging member 706 is engaged with pushrod 104A as illustrated in FIG. 7. Axial rotation of hub assembly 702 in a direction of rotation as indicated by arrow 126 causes axial translation of hub assembly 702 in an axial direction as indicated by arrow 712 away from distal housing 410 and towards proximal housing 412 of handle 112. More particularly, axial rotation of hub assembly 702 causes hub assembly 702 to move along a helical path of the thread of threaded outer surface 710 of pushrod 104A.

For example, hub assembly 702 is illustrated as being in a first axial position 730 adjacent distal housing 410 of handle 112 in FIG. 7. Axial rotation of hub assembly 702 in a direction as indicated by arrow 126 causes hub assembly 702 to move to a second axial position 732 between distal housing 410 and proximal housing 412 of handle 112 as illustrated in FIG. 8. Stated another way, axial rotation of hub assembly 702 causes axial translation of hub assembly 702.

Sheath 106 is coupled to hub assembly 702 as discussed further below. Accordingly, axial translation of hub assembly 702 causes axial translation, i.e., retraction, of sheath 106.

As a result, referring again to FIG. 1, a proximal end 128 of prosthesis 102, which is deployed first, is very gradually released. In this manner, the physician is allowed to verify the accuracy of the deployment position as prosthesis 102 initially engages the surrounding body lumen.

Further, after proximal end 128 of prosthesis 102 is deployed by retracting sheath 106 by rotating hub assembly 702 as discussed above, selectively engaging member 706 is selectively disengaged from pushrod 104A as illustrated in FIG. 8.

In accordance with one embodiment, by rotating slide ring 124A in a second direction opposite the first direction, e.g., clockwise, threaded surface 708 of selectively engaging member 706 is released (retracted) from threaded attachment with threaded outer surface 710 of pushrod 104A. Thus, rotation of slide ring 124A in the second direction disengages selectively engaging member 706, and thus hub assembly 702, from pushrod 104A.

Once disengaged, hub assembly 702 is slidably mounted on pushrod 104A. More particularly, hub assembly 702 is supported around pushrod 104A by sheath 106. Thus, hub assembly 702 is easily and quickly slid along pushrod 104A and longitudinal axis L of handle 112 without further rotation of hub assembly 702. By sliding hub assembly 702, sheath 106 is easily and quickly retracted thus rapidly completing deployment of prosthesis 102. Rapid deployment of prosthesis 102 facilitates faster procedure times, thus minimizing the period of time during which blood flow is occluded.

Sheath 106 is described above as being retracted by the combination of axial rotation of hub assembly 702 followed by sliding, i.e., axial translation, of hub assembly 702 along longitudinal axis L of handle 112. However, in an alternative embodiment, sheath 106 is retracted entirely by axial rotation of hub assembly 702. Further, in yet another embodiment, sheath 106 is retracted entirely by sliding of hub assembly 702 along longitudinal axis L of handle 112.

In yet another embodiment, hub assembly 702 is initially engaged with pushrod 104A. Sheath 106 is initially retracted by axial rotation of hub assembly 702. Hub assembly 702 is then disengaged from pushrod 104A. Sheath 106 is further retracted by sliding of hub assembly 702 along longitudinal axis L of handle 112. Hub assembly 702 is again engaged with pushrod 104A. For example, if the deployment force, e.g., friction, increases and the physician desires more mechanical advantage for further deployment of sheath 106. Sheath 106 is then further retracted by axial rotation of hub assembly 702. In the above manner, sheath 106 is retracted rapidly by sliding of hub assembly 702. However, at any time during retraction, hub assembly 702 can be engaged with pushrod 104A for more mechanical advantage and control of sheath 106.

As shown in FIG. 8, pushrod 104A extends between distal housing 410 and proximal housing 412 of handle 112. In one embodiment, distal housing 410 and proximal housing 412 are connected to and supported by a support member (not shown).

When disengaged, hub assembly 702 is easily and quickly slid along pushrod 104A of handle 112 from distal housing 410 to proximal housing 412. Since hub assembly 702 is coupled to sheath 106, axial translation of hub assembly 702 produces an axial translation of sheath 106. Overall, by sliding hub assembly 702, sheath 106 is easily and quickly retracted thus rapidly completing deployment of prosthesis 102.

For example, hub assembly 702 is illustrated as being at second axial position 732 between distal housing 410 and proximal housing 412 of handle 112 in FIG. 8. Axial translation of hub assembly 702 as indicated by arrow 720 causes hub assembly 702 to move to a third axial position 734 adjacent proximal housing 412 of handle 112 as indicated by the dashed lines in FIG. 8. Sheath 106 is coupled to hub assembly 702. Accordingly, axial translation of hub assembly 702 causes axial translation, i.e., retraction, of sheath 106.

FIG. 9 is a cross-sectional view of handle 112 taken at IX—IX of FIG. 7 in accordance with one embodiment of the present invention. FIG. 10 is a cross-sectional view of handle 112 taken at X—X of FIG. 9 in accordance with one embodiment of the present invention.

Referring now to FIGS. 9 and 10 together, hub assembly 702 includes hub 704. Hub 704 includes a cylindrical body 950 and selectively engaging member 706. In accordance with this embodiment, selectively engaging member 706 includes a first spring arm 902A and a second spring arm 902B, collectively spring arms 902. Spring arms 902 terminate at threaded surface 708.

In accordance with this embodiment, spring arms 902A, 902B include upper arms 952A, 952B and lower arms 954A, 954B connected together at elbows 956A, 956B. Upper arms 952A, 952B, lower arms 954A, 954B and elbows 956A, 956B are collectively referred to as upper arms 952, lower arms 954 and elbows 956, respectively.

First ends 958 of upper arms 952 are connected to cylindrical body 950. Second ends 960 of upper arms 952 are connected to first ends 962 of lower arms 954.

Second ends 964 of lower arms 954A, 954B include threaded surfaces 708A, 708B, respectively. Threaded surfaces 708A, 708B are collectively referred to as threaded surface 708.

Sheath 106 is rotationally mounted to hub 704 by a bearing 906. Bearing 906 allows hub assembly 702 including hub 704 to be rotating without imparting any rotation to sheath 106.

Slide ring 124A is rotationally mounted on hub 704. Illustratively, hub 704 includes flanges 908, 910, which fit into tracks 912, 914 of slide ring 124A. Thus, slide ring 124 is mounted on hub 704, yet, is capable of angular rotation relative to hub 704.

Referring now to FIG. 10, slide ring 124A is cylindrical and includes an inner surface 916. Tracks 912, 914 of slide ring 124A are formed in inner surface 916. Slide ring 124A further includes tabs 918A, 918B, collectively tabs 918, protruding inwards from inner surface 916.

Slide ring 124A is in a lock position 1002 in FIG. 10, i.e., is at a particular angular position relative to hub 704. When in lock position 1002, tabs 918 are engaged with and press inwards on spring arms 902. More particularly, elbows 956 of spring arms 902 are seated within notches 926A, 926B, collectively notches 926, of tabs 918A, 918B, respectively, when slide ring 124A is in lock position 1002.

This forces threaded surface 708 of spring arms 902 to engage threaded outer surface 710 of pushrod 104A. In this manner, hub assembly 702 is engaged with pushrod 104A.

To move hub assembly 702 relative to pushrod 104A, hub assembly 702 is rotated. The engagement of threaded surface 708 of selectively engaging member 706 to threaded outer surface 710 of pushrod 104A translates this axial rotation into axial translation of hub assembly 702.

In one embodiment, the direction in which slide ring 124A is rotated to engage hub assembly 702 with pushrod 104A, i.e., the first direction, is the same direction in which hub assembly 702 is rotated to retract sheath 106. In accordance with this embodiment, axial rotation of slide ring 124A in the first direction serves at least two purposes.

First, axial rotation of slide ring 124A seats spring arms 902 within notches 926 to engage threaded surface 708 of selectively engaging member 706 with threaded outer surface 710 of pushrod 104A. Second, once spring arms 902 are seated within notches 926, further axial rotation of slide ring 124A causes rotation of hub 704 and axial translation of hub assembly 702.

FIG. 11 is a cross-sectional view of handle 112 taken at XI—XI of FIG. 8 in accordance with one embodiment of the present invention. FIG. 12 is a cross-sectional view of handle 112 taken at XII—XII of FIG. 11 in accordance with one embodiment of the present invention.

Referring now to FIGS. 11 and 12 together, slide ring 124A is in an unlock position 1202 in FIG. 12, i.e., is at a second particular angular position relative to hub 704. For example, unlock position 1202 is 90 degrees from lock position 1002. In one embodiment, hub 704 is formed with stops 940A, 940B, collectively stops 940, which protrude outwards from hub 704 and engage tabs 918 to prevent slide ring 124A from being rotated past unlock position 1202.

When in unlock position 1202, tabs 918 are away from and are not engaged with spring arms 902. Spring arms 902 and, more particularly, upper arms 952, are resilient members. In one embodiment, when relaxed, spring arms 902 are positioned away from pushrod 104A. Stated another way, slide ring 124A places spring arms 902 under tension to engage spring arms 902 with pushrod 104A as illustrated in FIG. 10. However, when slide ring 124A is moved to unlock position 1202 as shown in FIG. 12, spring arms 902 return to their relaxed position adjacent inner surface 916 of slide ring 124A.

Thus, when slide ring 124A is in unlock position 1202 as shown in FIG. 12, threaded surface 708 of selectively engaging member 706 is disengaged from threaded outer surface 710 of pushrod 104A. This allows hub assembly 702 to be readily and easily slid along pushrod 104A as discussed above.

FIG. 13 is an enlarged cross-sectional view of the region XIII of pushrod 104A of FIG. 11 in accordance with one embodiment of the present invention. In accordance with this embodiment, threads 1302 of threaded outer surface 710 of pushrod 104A are buttress threads. Threads 1302 include angled surfaces 1304 in one direction and flat surfaces 1306 in the other.

Angled surfaces 1304 are at an angle to a plane perpendicular to longitudinal axis L. Stated another way, angled surfaces 1304 are angled relative to the direction normal to longitudinal axis L.

In contrast, flat surfaces 1306 are parallel to a plane perpendicular to longitudinal axis L. Stated another way, flat surfaces 1306 are in the direction normal to longitudinal axis L.

During rotation of hub assembly 702 as discussed above, referring now to FIGS. 9 and 13 together, threaded surface 708 of selectively engaging member 706 is forced against flat surfaces 1306 of pushrod 104A. In this manner, force is applied to selectively engaging member 706 in a direction parallel to longitudinal axis L thus causing axial translation of hub assembly 702. However, there is essentially no force applied to selectively engaging member 706 in the direction normal to longitudinal axis L. This essentially eliminates the possibility of spring arms 902 being forced apart and the associated slipping of hub assembly 702 on pushrod 104A.

However, in an alternative embodiment, threads 1302 are formed, for example, in a conventional profile, to impart force to selectively engaging member 706 in the direction normal to longitudinal axis L. For example, when a high load is imparted to hub assembly 702, e.g., when sheath 106 is stuck, spring arms 902 are forced apart and hub assembly 702 slips on pushrod 104A. This prevents damage to sheath 106 and complications in the deployment of prosthesis 112 (FIG. 1).

As discussed above, selectively engaging member 706 includes two spring arms 902, i.e., spring arms 902A, 902B, as shown in FIGS. 9 and 10. Spring arms 902 extend around and contact approximately two-thirds of the circumference of pushrod 104A. However, in one embodiment, selectively engaging member 706 includes only spring arm 902A or spring arm 902B, and not both. In yet another embodiment, selectively engaging member 706 includes three or more spring arms 902.

In yet other alternative embodiments, selectively engaging member 706 is a spring-loaded mechanism. This spring-loaded mechanism is biased such that it is engaged or disengaged with pushrod 104A when the spring-loaded mechanism is in its relaxed state. For example, the spring-loaded mechanism includes a screw that is engaged with pushrod 104A when the spring-loaded mechanism is in its relaxed position. The spring-loaded mechanism further includes a button, which is pressed to disengaged the screw. This button is integrated into hub assembly 702, or is mounted as a separate button or a trigger-type mechanism. However, other spring-loaded mechanisms are used in other embodiments.

Further, in one embodiment, a ratchet or pawl is used to prevent unintentional or undesirable axial rotation or axial translation. For example, a ratchet or pawl is used to prevent slide rings 124, 124A (FIGS. 2, 7) from axial rotation in the direction opposite arrow 126. As a further example, a ratchet or pawl is used to prevent slide ring 124, hub assembly 702 (FIGS. 4, 8) from moving backwards toward proximal housing 410.

This disclosure provides exemplary embodiments of the present invention. The scope of the present invention is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A delivery system comprising:
   a handle, wherein said handle comprises:
   a slide ring; and
   a slide within said slide ring, said slide being threadedly attached to said slide ring; and
   a sheath slidably and threadedly coupled to said handle.

2. The delivery system of claim 1 wherein axial rotation of said slide ring causes axial translation of said slide away from a distal end and towards a proximal end of said slide ring.

3. The delivery system of claim 2 wherein said sheath is coupled to said slide.

4. A delivery system comprising:
   a handle, wherein said handle comprises:
   a distal housing;
   a proximal housing;
   a slide shaft extending between said distal housing and said proximal housing;
   a slide ring; and
   a slide located within said slide ring, said sheath being coupled to said slide, said slide ring and said slide being slidably mounted on said slide shaft; and
   a sheath slidably and threadedly coupled to said handle.

5. A delivery system comprising:
   a handle comprising:
   a slide shaft comprising at least one slot;
   a slide ring;
   a slide threadedly attached to said slide ring comprising:
   an inner body inside said slide shaft;
   an outer body outside said slide shaft; and
   a coupler coupling said inner body to said outer body through said at least one slot,
   wherein said slide ring and said slide are slidably mounted to said slide shaft.

6. The delivery system of claim 5 further comprising a sheath coupled to said inner body.

7. The delivery system of claim 6 wherein said sheath comprises a pushrod lumen, said delivery system further comprising:
   a pushrod extending through said sheath; and
   a prosthesis over a distal end of said pushrod and restrained within a distal end of said sheath.

8. The delivery system of claim 7 wherein said prosthesis is deployed by sliding said slide ring down said slide shaft.

9. The delivery system of claim 7 wherein said prosthesis is deployed by rotating said slide ring.

10. The delivery system of claim 7 wherein said prosthesis is deployed by rotating and sliding said slide ring.

11. The delivery system of claim 5 wherein said slide ring comprises a threaded inner surface threaded to a threaded outer surface of said outer body.

12. The delivery system of claim 11 wherein rotation of said slide ring causes said slide to move along a helical path of said threaded inner surface of said slide ring.

13. A delivery system comprising:
   a sheath comprising a pushrod lumen;
   a pushrod extending through said sheath; and
   a handle comprising a hub assembly coupled to said sheath, said hub assembly comprising a selectively engaging member for selectively engaging and disengaging said hub assembly from said pushrod, wherein a threaded surface of said selectively engaging member is threadedly attached to a threaded outer surface of said pushrod when said hub assembly is engaged with said pushrod.

14. The delivery system of claim 13 wherein said hub assembly is engaged with said pushrod, and wherein axial rotation of said hub assembly causes axial translation of said sheath.

15. The delivery system of claim 13 wherein said hub assembly is slidably mounted to said pushrod when said hub assembly is disengaged from said pushrod.

16. The delivery system of claim 13 wherein said hub assembly is threadedly mounted to said pushrod when said hub assembly is engaged with said pushrod.

17. The delivery system of claim 13 wherein said selectively engaging member comprises at least one spring arm.

18. A delivery system comprising:
   a sheath comprising a pushrod lumen;
   a pushrod extending through said sheath; and
   a handle comprising a hub assembly coupled to said sheath, said hub assembly comprising a selectively engaging member for selectively engaging and disengaging said hub assembly from said pushrod, wherein said selectively engaging member comprises at least one spring arm and wherein a slide ring comprises at least one tab pressing on said at least one spring arm when said hub assembly is engaged with said pushrod.

19. A method of deploying a prosthesis comprising:
   restraining said prosthesis within a distal end of a sheath;
   rotating a slide ring of a handle in a first direction to initiate retraction of said sheath; and
   sliding said slide ring to further retract said sheath.

20. The method of claim 19 wherein said handle further comprises a slide threadedly attached to said slide ring, said rotating comprising moving said slide from a distal end of said slide ring and towards a proximal end of said slide ring.

21. The method of claim 20 wherein said sheath is coupled to said slide.

22. The method of claim 19 wherein said sliding comprises moving said slide ring from a distal housing and towards a proximal housing of said handle.

23. The method of claim 19 further comprising disengaging a hub assembly comprising said slide ring from a pushrod.

24. The method of claim 23 wherein said disengaging comprises rotating said slide ring in a second direction opposite said first direction.

25. The method of claim 23 wherein said sliding comprises sliding said slide ring along said pushrod.

26. The method of claim 19 further comprising disengaging a hub assembly comprising said slide ring from a threaded rod.

27. The method of claim 26 wherein said sliding comprises sliding said slide ring along said threaded rod.

28. The method of claim 26 wherein said threaded rod extends between a distal housing and a proximal housing of said handle.

29. A delivery system comprising:
 a sheath;
 a threaded rod comprising a lumen; and
 a hub assembly rotationally coupled to said sheath, said hub assembly comprising a selectively engaging member for selectively engaging and disengaging said hub assembly from said threaded rod, wherein a threaded surface of said selectively engaging member is threadedly attached to a threaded outer surface of said threaded rod when said hub assembly is engaged with said threaded rod.

30. The delivery system of claim 29 wherein said hub assembly is engaged with said threaded rod, and wherein axial rotation of said hub assembly causes axial translation of said sheath.

31. The delivery system of claim 29 wherein said hub assembly is slidably mounted to said threaded rod when said hub assembly is disengaged from said threaded rod.

32. The delivery system of claim 29 wherein said hub assembly is threadedly mounted to said threaded rod when said hub assembly is engaged with said threaded rod.

33. The delivery system of claim 29 wherein said threaded rod extends between a distal housing and a proximal housing of a handle.

34. The delivery system of claim 29 wherein said hub assembly is rotationally coupled to said sheath such that said hub assembly can be rotated without imparting any rotation to said sheath.

35. The delivery system of claim 29 wherein said hub assembly is rotationally coupled to said sheath by a bearing.

36. A delivery system comprising:
 a sheath;
 a threaded rod comprising a lumen; and
 a hub assembly rotationally coupled to said sheath, said hub assembly comprising a selectively engaging member for selectively engaging and disengaging said hub assembly from said threaded rod, wherein at least one arm of said selectively engaging member is threadedly attached to a threaded outer surface of said threaded rod when said hub assembly is engaged with said threaded rod.

37. The delivery system of claim 36 wherein said hub assembly is rotationally coupled to said sheath such that said hub assembly can be rotated without imparting any rotation to said sheath.

38. The delivery system of claim 36 wherein said hub assembly is rotationally coupled to said sheath by a bearing.

39. A delivery system comprising:
 a handle comprising:
 a slide shaft comprising at least one slot;
 a slide ring;
 a slide attached to said slide ring comprising:
 an inner body inside said slide shaft;
 an outer body outside said slide shaft; and
 a coupler coupling said inner body to said outer body through said at least one slot,
 wherein said slide ring and said slide are mounted to said slide shaft.

40. The delivery system of claim 39 further comprising a sheath coupled to said inner body.

41. The delivery system of claim 40 wherein said sheath comprises a pushrod lumen, said delivery system further comprising:
 a pushrod extending through said sheath; and
 a prosthesis over a distal end of said pushrod and restrained within a distal end of said sheath.

42. The delivery system of claim 41 wherein said prosthesis is deployed by sliding said slide ring down said slide shaft.

43. The delivery system of claim 41 wherein said prosthesis is deployed by rotating said slide ring.

44. The delivery system of claim 41 wherein said prosthesis is deployed by rotating and sliding said slide ring.

45. The delivery system of claim 39 wherein said slide is integral.

46. The delivery system of claim 39 wherein said coupler prevents rotation of said slide relative to said slide shaft.

47. A delivery system comprising:
 a sheath;
 a threaded rod comprising a lumen; and
 a hub assembly coupled to said sheath such that said hub assembly can be rotated without imparting any rotation to said sheath, said hub assembly comprising a selectively engaging member for selectively engaging and disengaging said hub assembly from said threaded rod, wherein a threaded surface of said selectively engaging member is threadedly attached to a threaded outer surface of said threaded rod when said hub assembly is engaged with said threaded rod.

48. A delivery system comprising:
 a sheath;
 a threaded rod comprising a lumen; and
 a hub assembly coupled to said sheath such that said hub assembly can be rotated without imparting any rotation to said sheath, said hub assembly comprising a selectively engaging member for selectively engaging and disengaging said hub assembly from said threaded rod, wherein at least one arm of said selectively engaging member is threadedly attached to a threaded outer surface of said threaded rod when said hub assembly is engaged with said threaded rod.

* * * * *